United States Patent [19]

Bouquet et al.

[11] Patent Number: 5,348,392
[45] Date of Patent: Sep. 20, 1994

[54] APPARATUS FOR MIXING AND DISPENSING A MULTICOMPONENT COMPOSITION

[75] Inventors: Philippe L. Bouquet, Mouans Sartoux, France; David Pocknell, Rhoose, Scotland; Werner Bruning, Engelskirchen, Fed. Rep. of Germany; Martina Dittrich-Duster, Engelskirchen, Fed. Rep. of Germany; Gunter Lamers, Engelskirchen, Fed. Rep. of Germany

[73] Assignee: Dow Corning France S.A., Valbonne, France

[21] Appl. No.: 133,538

[22] Filed: Oct. 7, 1993

Related U.S. Application Data

[63] Continuation-in-part of Ser. No. 849,851, Mar. 12, 1992.

[30] Foreign Application Priority Data

Mar. 13, 1991 [FR] France .................. 91 03016

[51] Int. Cl.$^5$ .................. B67D 5/52; G05D 11/00
[52] U.S. Cl. .................. 366/162; 222/82; 222/83.5; 222/137; 366/130; 366/184; 366/256
[58] Field of Search .................. 222/82, 83, 83.5, 87, 222/135, 136, 137; 366/129, 130, 139, 150, 161, 162, 184, 189, 255, 256, 332, 333, 334, 335

[56] References Cited

U.S. PATENT DOCUMENTS

| | | | |
|---|---|---|---|
| 2,954,144 | 9/1960 | Elam | 366/332 |
| 3,390,814 | 7/1968 | Creighton | 366/332 |
| 3,437,242 | 4/1969 | Pointras | 222/135 |
| 3,766,917 | 10/1973 | Wimmer | 222/136 |
| 3,972,331 | 8/1976 | Bolduc | 222/83 |
| 4,026,845 | 5/1977 | Kim et al. | 260/2.5 S |
| 4,550,125 | 10/1985 | Lee et al. | 521/117 |
| 4,613,630 | 9/1986 | Bauman et al. | 521/134 |
| 4,719,243 | 1/1988 | Pocknell | 521/91 |
| 4,969,747 | 11/1990 | Colin | 222/137 |

FOREIGN PATENT DOCUMENTS

| | | | |
|---|---|---|---|
| 1595 | 5/1979 | European Pat. Off. | 222/83.5 |
| 2589872 | 5/1987 | France . | |
| 1492581 | 11/1977 | United Kingdom . | |

Primary Examiner—Timothy F. Simone
Assistant Examiner—Terrence R. Till
Attorney, Agent, or Firm—Robert L. McKellar

[57] ABSTRACT

The apparatus is adapted to be held in one hand of an operator from mixing components of a composition packaged as two or more individually stable components of substantially equal volume and viscosity each in a receptacle having a closure made of a material which can be ruptured, and to dispense the mixed composition by a manual operation. The device comprises a mixing housing, separate chambers for the receptacles, piercing means for piercing the receptacles, plunger means for expelling a component from the chamber into the mixing region, a mixing element in the mixing region, and a passageway which contains means for actuating the mixing element and through which the mixed composition may be expelled from the mixing region. The construction and arrangement is such that relative movement of approach may be caused between the piercing means and the receptacles to rupture the receptacles, and between the plunger means and the mixing housing to urge the component into the mixing region, the mixing element may be actuated to mix the components in the mixing region, and relative movement of approach may be brought about between elements of the device to discharge the mixed composition through said passageway. The device is principally intended for mixing and dispensing of silicone foam to provide foamed dressings.

7 Claims, 4 Drawing Sheets

APPARATUS FOR MIXING AND DISPENSING A MULTICOMPONENT COMPOSITION

This is a continuation-in-part of copending application Ser. No. 07/849,851 filed on Mar. 12, 1992.

This invention is concerned with improvements in or relating to apparatus for mixing and dispensing a multi-component composition, for example a two part room temperature curable silicone foam.

Liquid curable compositions are available which flow and foam readily at room or slightly elevated temperature to provide a cured foam product. It has been proposed to employ foamable silicone based room temperature curable compositions for various purposes, including the preparation of medical dressings. Compositions for this purpose are disclosed, for example, in French Patent Specification 2589872. The compositions referred to therein comprise an organosilicon polymer including siloxane units providing a silicon-bonded hydroxyl group, an organosilicon polymer including siloxane units having a silicon-bonded hydrogen atom, a catalyst, for example a tin compound, and finely divided filler comprising silica which has been treated to render it hydrophobic. The compositions cure according to the scheme ≡SiOH+≡SiH→≡Si—O—Si≡+H$_2$.

Whilst satisfactory in many ways, the tin catalysed compositions disclosed in French Patent Specification 2589872 are regarded as less than satisfactory in that it has been suggested that the tin compound catalysts and/or derivatives thereof may have some undesirable toxic effects.

Formulations have been proposed for silicone rubber foams which do not use tin compound catalysts. Many of these formulations employ polydiorganosiloxanes having silicon-bonded vinyl groups available for reaction with polydiorganosiloxanes having silicon bonded hydrogen atoms and a platinum catalyst. The addition reaction which occurs is appropriate to yield chain extended or crosslinked elastomeric silicone products, but does not generate volatile materials for causing foaming in the curing composition. A foaming reaction may be induced in such formulations by inclusion of a polydiorganosiloxane having silicon-bonded hydroxyl groups among the ingredients with a view to reaction with the polydiorganosiloxane having silicon-bonded hydrogen atoms as more fully described for example in U.S. Pat. No. 4,026,845, with or without the presence of water or an aliphatic alcohol as more fully described for example in U.S. Pat. No. 4,613,630, or by inclusion in the composition of a volatile blowing agent as more fully described for example in U.S. Pat. No. 4,550,125. Hitherto, our attempts to employ foamable compositions based on polydiorganosiloxanes having silicon bonded hydrogen atoms and silicon-bonded vinyl groups have not resulted in compositions which cure and foam suitably to form foamed dressings in situ on a patient's body. In particular they do not always cure satisfactorily in contact with wet wound surfaces and may even exhibit an uncured, liquid surface layer; some cure too slowly for convenient use and others do not yield a foam of desirably low density and structure for convenient use as an in situ formed medical dressing. Desirably, compositions intended for in situ provision of medical dressings are curable at room temperatures of the order of 20° C.±4° C. within 100 seconds ±40 seconds of application to the body to yield a foam of uniform fine pores having a density between 100 Kg/m$^3$ and 400 Kg/m$^3$ and having a major proportion of open cells.

We have now found that a foam forming composition suitable for use in preparation of in situ formed dressings may comprise two components having similar viscosities each of which may be stored in a receptacle designed to be ruptured to release the components for admixture. Suitable foam forming compositions include those comprising one or more polydiorganosiloxanes having not less than three alkyl-hydrogensiloxane units per molecule, (B) one or more polydiorganosiloxanes having not less than two siloxane units of the formula $$R_aR'_bSiO_{\frac{(4-(a+b))}{2}}$$

in which R represents a monovalent hydrocarbon group containing 1 to 20 carbon atoms, R' represents an unsaturated hydrocarbon group, a has the value 0, 1 or 2 and b has the value 1 or 2, (C) a liquid alcohol, (D) a fluorinated silicone foam stabilizing material and (E) a platinum catalyst for promoting reaction between the components.

It is an object of this invention to provide an improved hand held device suitable for the storage, mixing and dispensing of silicone compositions whether foamable or not, especially those which are packaged as separate components of substantially equal viscosities and in substantially equal volumes.

The present invention provides in one of its aspects a mixing and dispensing device adapted to be held in one hand of an operator for mixing together the components of a silicone composition packaged in the form of two or more individually stable components of substantially equal volume and viscosity each in a receptacle, and to dispense the mixed composition by a manual operation, the device comprising a mixing housing in which there is a mixing region into which the components of the multi-component composition may be introduced and mixed together, separate chambers each comprising one of said receptacles or forming a receptacle having a closure made of a material which can be ruptured, each chamber communicating with the mixing region, piercing means which is arranged so that when it is desired to release a component from its receptacle the piercing means may be caused to pierce the receptacle, plunger means for expelling a component from the chamber by forcing it into the mixing region, a mixing element located in the mixing region for mixing the components of the composition, and a passageway which contains means for actuating the mixing element and through which the mixed composition may be expelled from the mixing region, the construction and arrangement being such that when it is desired to mix and dispense the composition relative movement of approach may be caused between the piercing means and the receptacles to bring about rupture of the receptacles, relative movement of approach may be brought about between the plunger means and the mixing housing to urge the component into the mixing region, the mixing element may be actuated to mix the components in the mixing region, and relative movement of approach may be brought about between elements of the device to discharge the mixed composition from the device through said passageway.

Two devices according to the invention are hereinafter described to illustrate the invention. These illustrative devices are adapted to be held in one hand of an operator for mixing together the components of a multi-component composition and for dispensing the mixed composition by manual operation. Each illustrative device has a mixing housing in which there is a mixing region and chambers for housing the parts of the composition. In the illustrative devices the chamber support comprises two cylindrical chambers, the axes of which are parallel and located at either side of, and parallel to, a centre line of the chamber support. The chambers are located at approximately 180° about the axis of the mixing housing. Such embodiments are useful for the mixing and dispensing of two component compositions. The parallel, that is side-by-side, location of the two chambers facilitates loading of the components into the chambers particularly when discrete envelopes of components are used.

In a device according to the invention, the components are expelled from their chambers into the mixing region by action of the plunger means. Preferably, the plunger means is arranged so that a single actuation of the plunger means causes delivery of the desired proportions of the components from the chambers simultaneously. The illustrative devices have a plunger for each chamber and two plungers which are rigidly connected together and which are mounted for simultaneous sliding movement within the chambers.

A device according to the invention has piercing means which may be caused to penetrate a container present in the chamber. Although the means for piercing the container may be formed so as to completely cut away part of the container, for example by cutting a circular shape, it is preferred that the means for piercing the container is arranged so that the part of the container which is cut remains attached to the container and so does not pass into the mixing housing with the components of the composition. The means for piercing the container may for example, cut a part of, but not a complete, circular shape. The means for piercing may comprise a needle or blade. In the first illustrative device, the means for piercing the envelope is a circular or part elliptical knife blade and is formed integrally with the chamber support. Ports extend through the centre of the piercing means and communicate between the chambers and the mixing region. In the second illustrative device the means for piercing the envelope is provided by knife means supported on the mixing element.

A device according to the invention is provided with means for rotating, reciprocating or otherwise agitating the mixing element to effect mixing of the combined components. In the illustrative devices the mixing element is releasably secured to a mixer rod which extends through the device and has a handle by means of which the mixing element may be moved reciprocally in the mixing region for mixing the components in the mixing region. The mixer rod is releasably secured to the mixing element by a screwthread connection. The mixing element is preferably restrained from rotation in the mixing housing about the axis of the mixing housing so that the mixer rod can be removed from the device after mixing has been accomplished, for example by provision of splines or abutments or by arranging that the relative shapes and sizes of the mixing housing and the mixing element are such as to restrain such rotation. In the first illustrative device, the mixing housing and the mixing element are oval in shape and the narrowest cross-sectional width of the mixing housing is narrower than the widest cross-sectional width of the mixing element so that the mixing element cannot fully rotate in the mixing housing. In the second illustrative device splines are used for the same purpose.

A device according to the invention is preferably sealed against ingress of foreign matter.

The first illustrative device comprises a) a mixing housing comprising a base having an interior surface and a wall having an interior wall surface;

b) a chamber support providing parallel chambers, one for each component of the multi-component composition, the chamber support having a base and a wall, each having an exterior surface, the chamber support being slidable in the housing and the exterior surface of the base of the chamber support and the interior surfaces of the housing base and housing wall being such that together they define a mixing region into which the components of a multi-component composition may be introduced and mixed together, each chamber comprising a wall extending from an interior surface of the base of the chamber support and the chamber wall having an interior surface and each chamber communicating with the mixing region via a port in the base of the chamber support;

c) piercing means which is arranged so that when it is desired to release a component from a receptacle located in the chamber the piercing means may be caused to pierce the receptacle;

d) plunger means slidably engaged with the interior wall surface of each chamber suitable for expelling a component from the chamber into the mixing region;

e) a perforate mixing element located in the mixing region;

f) means for causing movement of the mixing element in the mixing region for mixing the components of the composition, and g) a passageway located between the chambers and communicating with the mixing region at one end and providing a nozzle at its other end so that the mixed composition may be expelled from the mixing region via the passage-way upon bringing about relative movement of approach between the mixing housing and the chamber support.

The second illustrative device comprises a mixing and dispensing device adapted to be held in one hand of an operator for mixing together the components of a multi-component composition and for dispensing the mixed composition by manual operation comprising a) a mixing housing comprising a base having an interior surface and a wall having an interior wall surface;

b) a chamber support having parallel chambers, one for each component of the multi-component composition, the chamber support being fixed to the wall of the mixing housing, such that together they define a mixing region into which the components of a multi-component composition may be introduced and mixed together, each chamber communicating with the mixing region via a port in the chamber support;

c) a perforate mixing element located in the mixing region;

d) piercing means which is arranged so that when it is desired to release a component from a chamber the piercing means may be caused to pierce a retaining surface to release the component from the chamber;

e) plunger means slidably engaged with the interior wall surface of each chamber suitable for expelling a component from the chamber into the mixing region;

f) a passageway communicating with the mixing region at one end and providing a nozzle at its other end so that the mixed composition may be expelled from the mixing region via the passageway upon bringing about relative movement of approach between the mixing housing and the chamber support, and g) means for causing movement of the mixing element in the mixing region for mixing the components of the composition.

A device according to the invention is particularly suitable for use for mixing and dispensing sterile components of a composition which may be supplied in sterile discrete receptacles. Thus, for example, the device may be used for the sterile dispensing of compositions intended for medical use, for example as medical dressings on, or for use on, the human or animal body.

There now follows a detailed description, to be read with the accompanying drawings, of the illustrative devices and a modified form of the first illustrative device.

Figure 1:
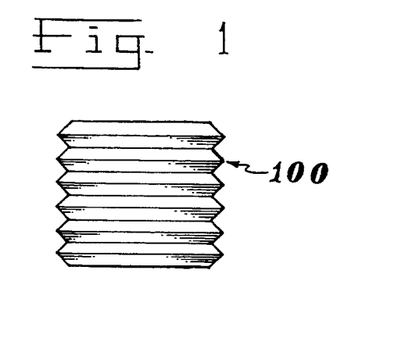
FIG. 1 is a side elevation of a receptacle containing one component part of a composition.
Figure 2:
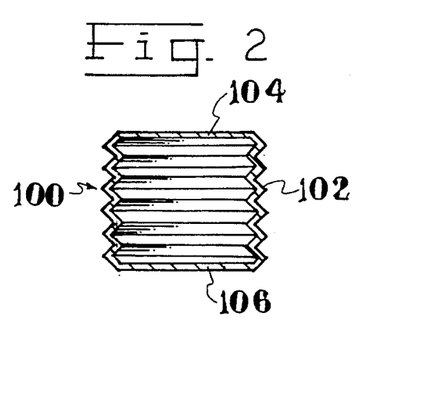
FIG. 2 is a section of the receptacle shown in FIG. 1.

An example composition was prepared comprising two components of substantially equal viscosity and volume of a silicone composition capable of cure at room temperature to provide a fine pored foam. For use in the first illustrative device, the component parts A and B were packaged separately in receptacles having the shape of a cylindrical bellows (100 FIGS. 1 and 2). Each bellows was formed from polypropylene and comprises corrugated walls (102) and reinforced upper (104) and lower (106) surfaces. The construction and arrangement of each receptacle is such that when the receptacle is perforated to release the component, a comparatively light pressure is sufficient to cause controlled collapse of the receptacle in the direction of its axis so that the bellows may be emptied.

Figure 4:
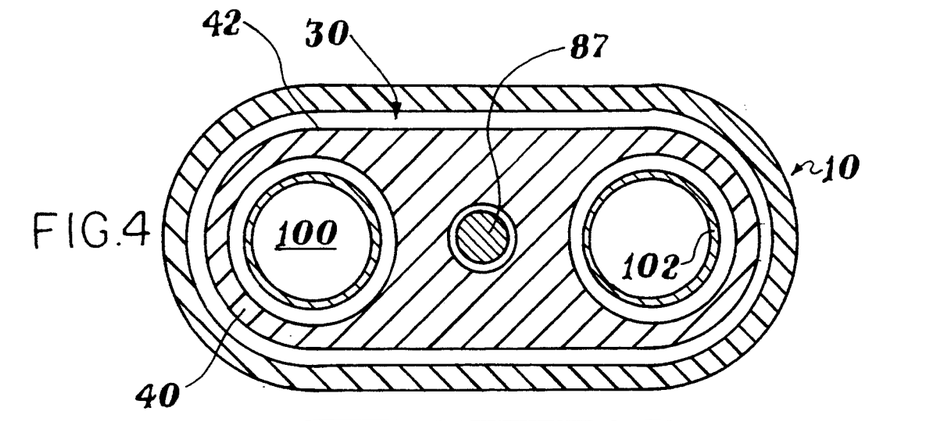
FIG. 4 is a section taken substantially on the line X—X of FIG. 3.
Figure 5:
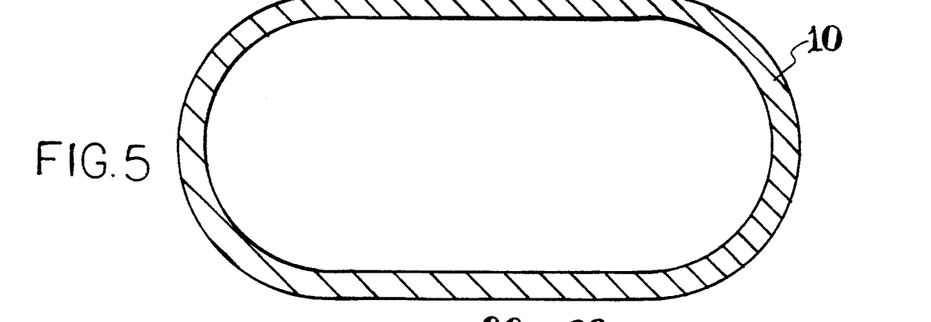
FIG. 5 is a section taken substantially on the line Y—Y of FIG. 3.

The first illustrative device comprises a mixing housing (10) (FIGS. 3, 4 and 5) which has a generally oval configuration, having parallel sides and rounded ends. The mixing housing (10) comprises a base (12) having a continuous interior base surface (14) (FIG. 3) and a wall (16) upstanding from the base (12) which has an interior wall surface (18). A chamber support (30) is mounted for sliding movement in the mixing housing (10). The chamber support (30) comprises two circular chambers (32 and 34) the axes of which are parallel and located at either side of and parallel to a centre line of the chamber support. The chamber support (30) has a base (36) having an exterior base surface (38) and a wall (40) upstanding from the base (36) which has an exterior wall surface (42). The wall (16) of the mixing housing (10) has an inwardly extending lip (20) at its upper end (as viewed in FIG. 3) which extends entirely around the upper edge of the wall (16) and carries a sealing ring (22). The wall (40) of the chamber support (30) has a shape such that the exterior wall surface (42) engages firmly with the sealing ring (22) so that a seal is provided between the walls of the chamber support and the mixing housing. An abutment (44) extends around the chamber support (30) at its base and serves to stabilise the chamber support in the mixing housing and to cooperate with the lip (20) to prevent the mixing housing and chamber support from becoming separated inadvertently. The exterior surface (38) of the base of the chamber support (30), the interior surface (14) of the base (12) of the mixing housing (10) and the interior surface (18) of the wall (16) of the mixing housing together define a mixing region (80).

Figure 3:
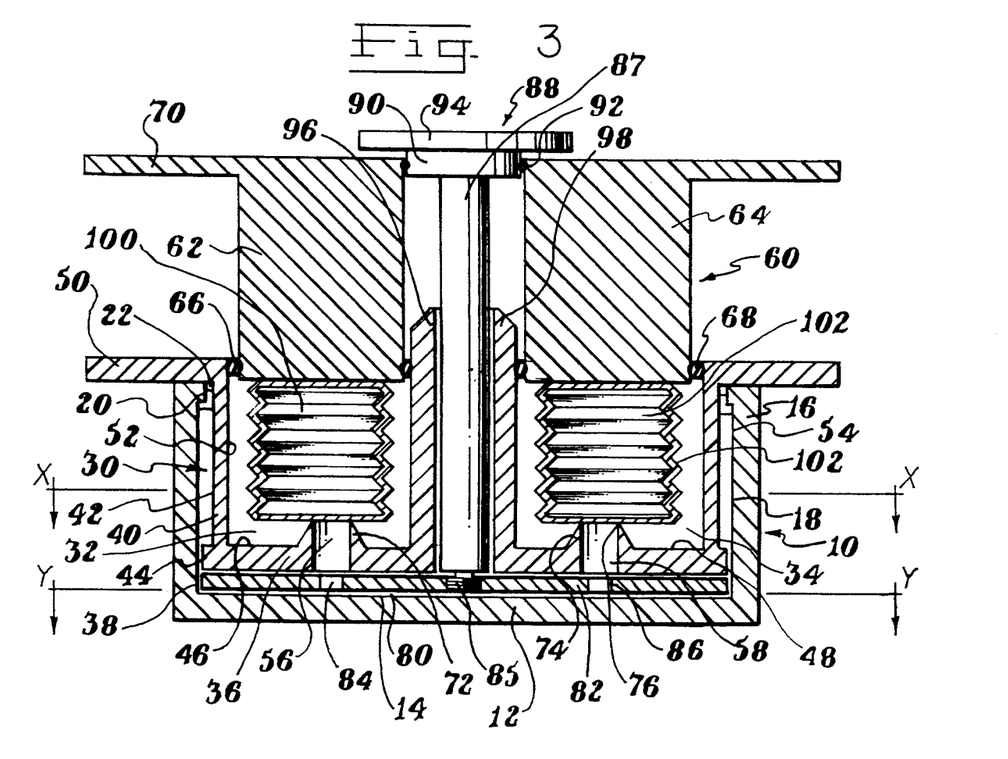
FIG. 3 is a section of the first illustrative device.

The device has plunger means (60) comprising two plungers (62, 64) which are rigidly connected together and which are mounted for simultaneous sliding movement within the chambers (32, 34 respectively). Between each chamber (32, 34) and its plunger (62, 64) there is a sealing ring (66, 68). Each chamber (32, 34) is circular in section and is defined by an interior surface (46, 48) of the base (36) of the chamber support, a generally cylindrical interior wall surface (52, 54) in the chamber support (30) and a surface of its plunger. The chambers (32) and (34) communicate with the mixing region (80) via ports (56, 58) in the base of the chamber support (30). The extent to which each plunger (62, 64) may penetrate its chamber is limited by flanges (50) on the chamber support (30) and flanges (70) on the plunger means (60). These flanges are useful for handling the device and for moving its parts relative to one another. The chambers (32, 34) are shaped to receive a container (100, 102). The interior base surface (46, 48) of each chamber has piercing means provided by an upstanding conical piercing element (72, 74) formed integrally with the chamber support (30). The ports (56, 58) extend through the piercing elements (72, 74 respectively) centrally so that the piercing elements are provided with a circular cutting edge (76) disposed normal to the axis of its chamber.

A perforate mixing element (82) is contained within the mixing region (80) and has holes (84, 86) therein. The mixing element (82) is releasably secured to a mixer rod (84) by a screw-thread connection (85). The mixer rod (84) has a protuberance (88) at the end opposite to that to which the mixing element (82) is connected. A lower (as viewed in FIG. 3) portion (90) of the protuberance (88) closes an aperture in the plunger means (60) between the plungers (62, 64). A sealing ring (92) is located between the lower portion (90) and the plunger means. An upper (as viewed in FIG. 3) portion (94) of the protuberance (88) serves as a handle for the mixer rod by means of which the mixing element may be moved reciprocally in the mixing region and by means of which the mixer rod may be unscrewed from the mixing element.

The mixer rod (84) passes through a passageway (96) formed in the chamber support (30). The passageway (96) is located substantially centrally between the chambers. One end of the passageway (96) communicates with the mixing region (80) and its opposite end provides a nozzle (98).

Figure 7:
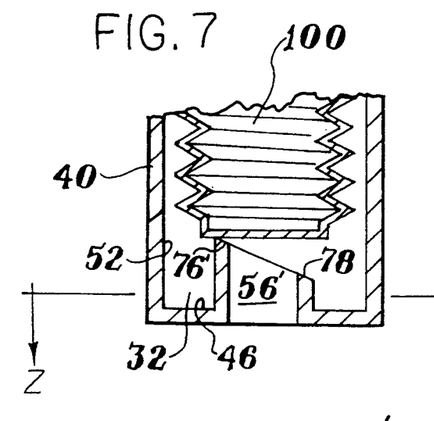
FIG. 7 is a section of a chamber of the modified form of the first illustrative device containing an intact receptacle in the form of a bellows.
Figure 8:
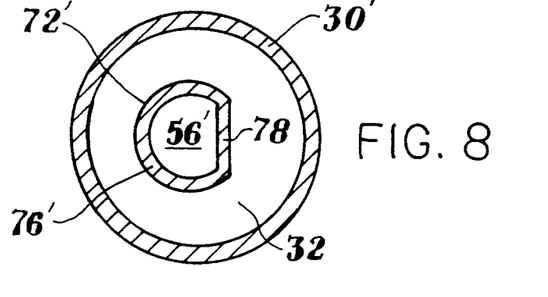
FIG. 8 is a section taken substantially on the line Z—Z of FIG. 7.
Figure 9:
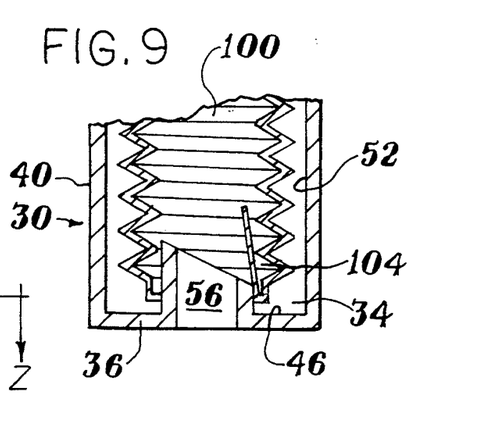
FIG. 9 is a section similar to FIG. 7 but showing the receptacle during operation of the device.

The modified form of the first illustrative device is the same as the first illustrative device except that the piercing means is of a different design. In the modified form (FIGS. 7, 8 and 9) the piercing means is provided by an upstanding piercing element in the form of a rib (72', 74' not shown ) formed integrally with the chamber support (30') and which describes a closed figure through which the port (56' and 58' not shown) extends. Each piercing element (72', 74') comprises a part elliptical cutting edge (76') which is inclined to the axis of its chamber, and a straight, blunt edge (78).

Figure 6:
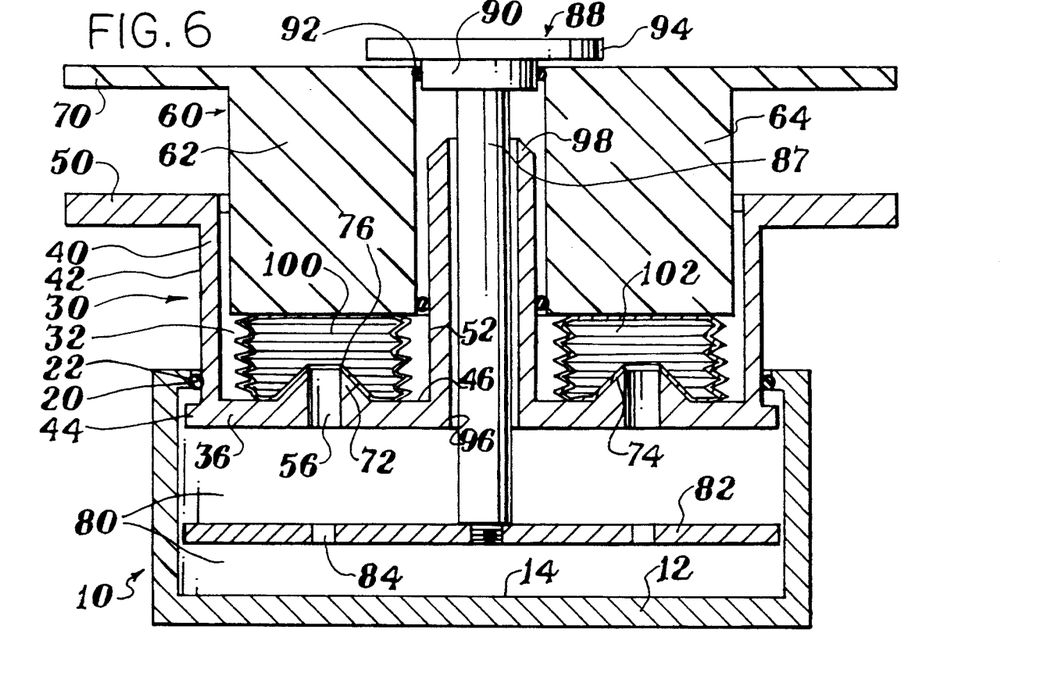
FIG. 6 is a section similar to FIG. 3 but showing a portion of the first illustrative device during operation of the device.

Operation of the first illustrative device, using the two components of the two component room temperature curable composition which are received in two separate receptacles (100, 102) will now be described. When assembled with the receptacles in the chambers (32, 34) and prior to use, the parts of the device occupy the positions shown in FIG. 3. In this condition, the mixing element (82) is trapped between the mixing housing (10) and the chamber support (30) with nothing present in the mixing region other than the mixing element. The plungers (62, 64) rest upon the receptacles and exert no compressive force on them. The mixer rod (84) is in threaded connection with the mixing element and the lower portion (90) of the protuberance closes the plunger means against ingress of air and foreign matter. When it is desired to operate the device, it may be held in one hand and the flanges (50 and 70) drawn towards each other whereby the plungers (62, 64) are caused to penetrate the chambers to compress the receptacles, and the mixer rod (94) is pushed through the chamber support (30). As the receptacles are compressed in the chambers, they are pierced by the piercing elements (72 and 74). Further penetration of the plungers into the chambers causes the expulsion of the contents of the receptacles (100, 102) into the mixing region (50). FIG. 6 shows the device when most of the contents of the receptacles (100, 102) have been expelled into the mixing region. When expulsion of the components into the mixing region has been completed, the mixer rod (84) is reciprocated for about 15 seconds to cause the mixing element to move in the mixing region for mixing the components of the composition in the mixing region. The mixer rod (84) is disconnected by unscrewing from the mixing element (82) and removed from the device. The mixed contents of the mixing housing (50) are expelled from the device by holding the flanges (50 and 70) and pushing the mixing housing (10) toward the chamber support (30) so that the mixed contents from the mixing region (80) are urged to pass along the passageway (96) and through the nozzle (98).

When using the modified form of the first illustrative device (FIGS. 5, 6 and 7) when the receptacles (100, 102) are pushed onto the means for piercing the receptacle, the partially elliptical cutting edge (76') cuts the receptacle but the part of the receptacle which abuts against the straight, blunt edge (78) is not cut and so a flap (104) is formed. In this way the possibility is avoided that a disc cut from the receptacle may contaminate the composition.

Figure 12:
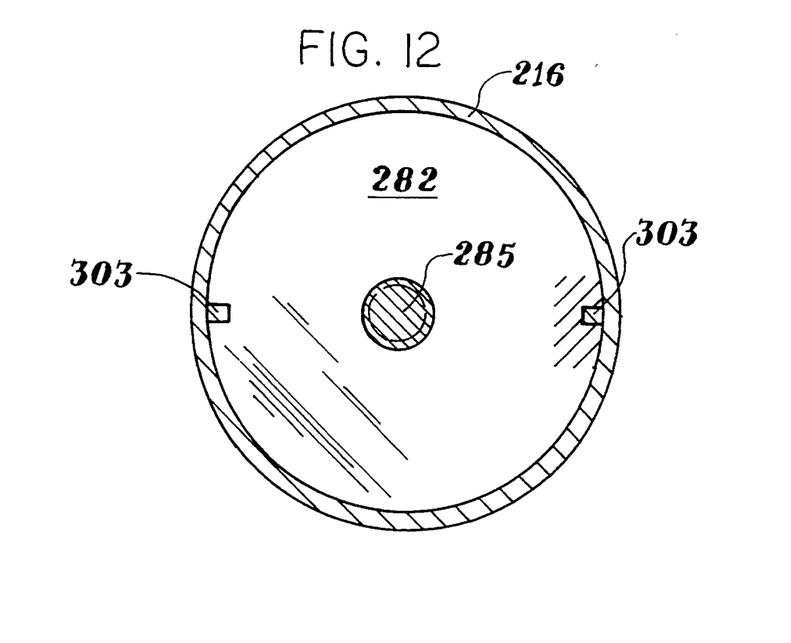
FIG. 12 is a section taken substantially on the line A—A of FIG. 10.

The second illustrative device (FIGS. 10—12) comprises a mixing housing (210) which has a generally circular configuration and comprises a base (212) having an interior base surface (214) and which is fixed to a cylindrical wall (216) upstanding from the base (212) which has an interior wall surface (218). An upper end (as viewed in FIG. 10) portion of the mixing housing is closed by a circular wall which provides a chamber support (230). The chamber support is formed with circular openings (256, 258) each of which is bounded by an upstanding flexible locating lug in the form of a ring (229, 231). Each ring is adapted to receive a neck (233, 235) of a generally cylindrical receptacle or chamber (232, 234) so that the axes of the chambers are parallel and located at either side of and parallel to a centre line of the chamber support (230). Each neck is provided with clip means which co-operate with the rings (229, 231) to secure the chambers (232, 234) to the support (230). The chamber support (230) has an exterior base surface (236) disposed towards the mixing housing. The base surface (236) of the chamber support (230), the interior surface (214) of the mixing housing (210) and the interior surface (218) of the wall (216) of the mixing housing together define a mixing region (280). The base (230) is formed to provide ports (256, 258) communicating between the chambers and the mixing region.

The chambers (232, 234) each contain one of the component parts of the illustrative composition. They are sealed by piston elements (263, 265) configured to mate with the interior of the neck (233, 235) of the chamber and sealed at their lower ends by an aluminium foil stretched across an opening in the neck. During storage the piston elements are located at the top (as viewed in FIG. 10) of the chambers with composition sealed in the chambers between the piston elements and the aluminium foil. Sealing rings (266, 268) are located between the piston elements and the interior walls of the chambers. Upper end portions of the chambers are received in a flange element (250) adapted to be gripped by the fingers of an operator.

Figures 10, 11:
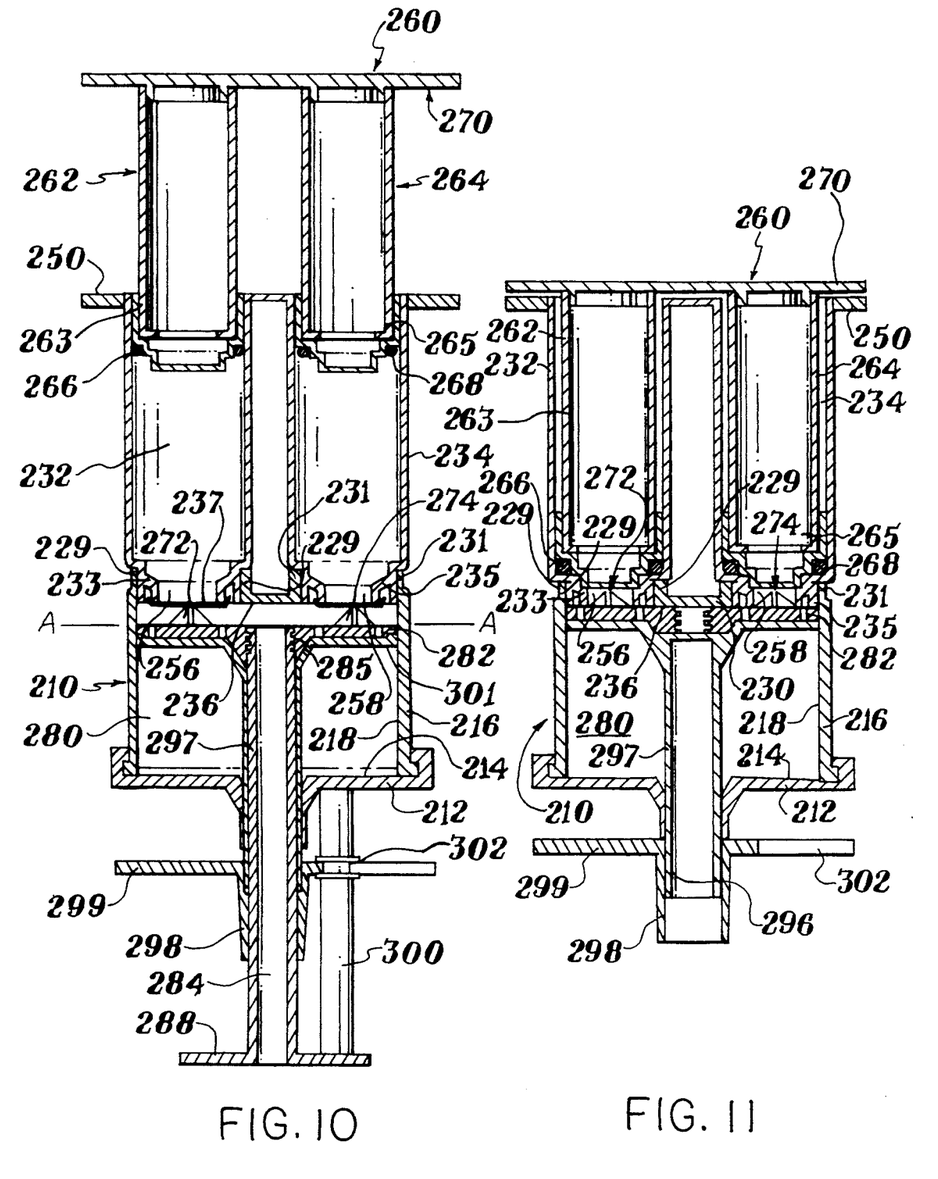
FIG. 10 is a sectional view of the second illustrative device.
FIG. 11 is a section similar to FIG. 10, but showing the second illustrative device during operation.

The device has plunger means (260) comprising two plungers (262, 264) which are rigidly connected together and which are mounted in the piston elements (263, 265) and arranged for simultaneous advancement towards the mixing housing to urge the piston elements axially into the chambers (232, 234) towards the necks thereof simultaneously.

The chambers (232, 234) are located to communicate with the mixing region (280, not shown) via the ports (256, 258) in the base of the chamber support (230). The extent to which each plunger (262, 264) may penetrate its chamber is limited by the piston elements and the necks of the chambers and by the flange (250) on the chamber support (230) and flanges (270) on the plunger means (260). These flanges are useful for handling the device and for moving its parts relative to one another.

A perforate mixing element (282) is contained within the mixing region (280) and is releasably secured to a mixer rod (284) by a screw-thread connection (285). Piercing means in the form of upstanding conical piercing elements (272,274) are provided on the mixing element for perforating the foils (237) blocking the ports (256, 258). The mixer rod (284) is housed in a passageway (296) in a tube (297) which extends through the mixing housing (210) and which carries a piston (301) at its end situated in the housing 210). The tube also carries a nozzle (298) having flanges (299). The passageway (296) is located substantially centrally between the chambers. One end of the passageway (296) communicates with the mixing region (280) and its opposite end extends into the nozzle (298). Outer end portions of the mixer rod are formed with flange portions (288).

Prior to use the mixing element (282) is located between the mixing housing (210) and the chamber support (230) with the piercing elements drawn away from the chambers sufficiently to avoid contact between the piercing elements and the aluminium foils of the chambers. A locking device is provided which comprises a separator rod (300) located parallel to the rod (284) and in contact with the base (212) and a flange (288) and extends through a slot (302) in a flange (299). The rod has lugs thereon which are engaged at either side of the flange (299). The locking device serves to ensure the mixing element is not moved inadvertently relative to the chambers. In order to load the device two chambers (each containing a component part of the silicone composition) are clipped into place on the support (230). The plungers are located in the piston elements. The device is stored with the plungers (262, 264) resting upon the piston elements and exerting no compressive force on them. The mixer rod (284) is in threaded connection with the mixing element and the locking device is in place. When it is desired to operate the device it may be held in one hand and the separator rod (300) of the locking device removed. The rod (284) may be moved to push the mixing element (282) towards the chambers (232,234) to an extent sufficient for the piercing elements (272, 274) to pierce the foils. Then the flanges (250, 270) may be drawn towards each other whereby the plungers (262, 264) are caused to push the piston elements down the chambers to urge their contents into the mixing region (280). When expulsion of the components into the mixing region has been completed the mixer rod (284) is reciprocated to cause the mixing element to reciprocate in the mixing region to mix the components of the composition in the mixing region. The mixer rod (284) is disconnected by unscrewing from the mixing element (282) and removed from the device. The mixed contents of the mixing housing (210) are expelled from the device by holding the flanges (270, 299) and moving the nozzle (298) and thus the tube (297) and mixing element towards the chamber support (230) so that the mixed contents from the mixing region (280) are urged to pass along the passageway (296) and through the nozzle (298).

That which is claimed is:

1. A mixing and dispensing device for mixing together the components of a silicone composition packaged in the form of two or more individually stable components of substantially equal volume and viscosity each in a separate receptacle, and to dispense the mixed composition by a manual operation, the device comprising in combination:
   a housing having a bottom, side walls, and an open top;
   a unitary support means, said support means having a bottom, an essentially circular exterior side wall and an essentially circular interior side wall and being comprised generally of two separate chambers each having a bottom, an open top, a single perforation through said bottom and an open port having a top end and a bottom end, and essentially aligned with the single perforation in each said chamber and which leads into the interior of the housing via said bottom end of said port, said port terminating at an upper end of said port in a piercing component, said support means being slidably contained in said housing through the housing top, said support means having a bore through a center of said support in the sliding direction, essentially separating the two separate chambers;
   said support means having adapted thereto, a mixer rod, said mixer rod having an enlarged upper end; said mixer rod projecting through the center bore and slidable therein, said mixer rod terminating in a threaded end opposite the enlarged upper end;
   said mixer rod having attached to said threaded end, a mixing element, said mixing element being located beneath the support means, but contained in the housing;
   the bottom and side wall of the housing, in combination with the bottom and side walls of the support means forming a mixing chamber located beneath said support means and contained in said housing;
   a plunger means comprising two adjacent, parallel plungers each having a flanged top which plungers are rigidly connected to each other at their tops and are adaptable for insertion into the tops, respectively, of the two separate chambers of the support means, said plungers containing slidably therebetween, the mixer rod;
   the interior wall of said support means being elongated such that said support forms a nozzle for exiting composition after said composition is mixed, and after the mixer rod has been removed from the mixing element.

2. A mixing and dispenser device of claim 1 wherein there is also present a component receptacle contained in each separate chamber of said support means such that the component receptacles are essentially adjacent and parallel to each other.

3. A device according to claim 1 wherein the chamber support comprises two cylindrical chambers the axes of which are parallel and located at either side of, and parallel to, a centre line of the chamber support and the plunger means are mounted for simultaneous sliding movement within the chambers.

4. A device according to claim 1 comprising,
   a) mixing housing comprising a base having an interior surface and a wall having an interior wall surface;
   b) a chamber support providing parallel chambers, one for each component of a multi-component composition, the chamber support having a base and a wall, each having an exterior surface, the chamber support being slidable in the housing and exterior surface of the base of the chamber support and the interior surfaces of the housing base and housing wall being such that together they define a mixing region into which the components of the multi-component composition may be introduced and mixed together, each chamber comprising a wall extending from an interior surface of the base of the chamber support and the chamber wall having an interior surface and each chamber communicating with the mixing region via a port in the base of the chamber support;
   c) piercing means which is arranged to release a component from a receptacle in the device the piercing means is caused to pierce the receptacle;
   d) plunger means slidably engaged with the interior wall surface of each chamber suitable for expelling a component from the chamber into the mixing region;
   e) a perforate mixing element located in the mixing region;

f) means for causing movement of the mixing element in the mixing region for mixing the components of the composition, and g) a passageway located between the chambers and communicating with the mixing region at one end and providing a nozzle at an opposite end so that the mixed composition is expelled from the mixing region via the passageway upon bringing about relative movement of approach between the mixing housing and the chamber support.

5. A device according to claim 3 wherein the means for piercing a receptacle is arranged so that the part of the receptacle which is cut remains attached to the receptacle.

6. A device according to claim 1 comprising a) a mixing housing comprising a base having an interior surface and a wall having an interior wall surface;

b) a chamber support having parallel chambers, one for each component of the multi-component composition, the chamber support being fixed to the wall of the mixing housing, such that together they define a mixing region into which the components of a multi-component composition may be introduced and mixed together, each chamber communicating with the mixing region via a port in the chamber support;

c) a perforate mixing element located in the mixing region;

d) piercing means which is arranged to release a component from a chamber the piercing means is caused to pierce a retained surface of said chamber to release the component from the chamber;

e) plunger means slidably engaged with the interior wall surface of each chamber suitable for expelling a component from the chamber into the mixing region;

f) a passageway communicating with the mixing region at one end and providing a nozzle at an opposite end so that the mixed composition is expelled from the mixing region via the passageway upon bringing about relative movement of approach between the mixing housing and the chamber support, and g) means for causing movement of the mixing element in the mixing region for mixing the components of the composition.

7. The device according to claim 1 wherein said composition is used to form medical dressings.

* * * * *